United States Patent [19]

Pederson, Jr. et al.

[11] 4,192,988
[45] Mar. 11, 1980

[54] ELECTRICALLY HEATED THERMAL MICROBIAL DRAIN BARRIER

[75] Inventors: Paul D. Pederson, Jr., Minnetonka; Keith A. Ufford, Osseo; Lawrence V. Nelson, Anoka, all of Minn.

[73] Assignee: Foto-Mark, Inc., Egan, Minn.

[21] Appl. No.: 814,644

[22] Filed: Jul. 11, 1977

[51] Int. Cl.$^2$ .................. H05B 1/00; A61L 1/00; E03C 1/28
[52] U.S. Cl. .................. 219/201; 4/206; 134/19; 138/33; 219/301; 219/535; 422/22
[58] Field of Search ............... 219/200, 201, 280, 281, 219/296, 299, 297, 300, 301, 302, 535, 311, 543; 4/255, 191, 206, 207; 138/33; 134/5, 19; 285/41

[56] References Cited

U.S. PATENT DOCUMENTS

| | | | |
|---|---|---|---|
| 2,085,470 | 6/1937 | Pieper | 219/301 X |
| 2,452,367 | 10/1948 | Gangloff | 219/201 |
| 3,050,608 | 8/1962 | De Woody | 219/201 |
| 3,105,136 | 9/1963 | Ashenfarb | 219/300 |
| 3,126,469 | 3/1964 | Feldmann et al. | 219/297 X |
| 3,985,994 | 10/1976 | Eloranta et al. | 219/301 X |

FOREIGN PATENT DOCUMENTS

| | | | |
|---|---|---|---|
| 2306479 | 8/1973 | Fed. Rep. of Germany | 219/301 |
| 1316098 | 5/1973 | United Kingdom | 219/535 |

OTHER PUBLICATIONS

"Pyrex Brand E-C Coated Tubes For Laboratory Heating Jackets", Jun. 1954, Corning Glass Works, Corning, N.Y.

*Primary Examiner*—A. Bartis
*Attorney, Agent, or Firm*—James R. Haller

[57] ABSTRACT

A microbe drain barrier for insertion in the drain of a sink or the like to prevent microorganisms from reentering the sink from the drain. The barrier includes a length of thin-walled heat-resistant, electrically non-conductive tubing having a heat conductivity in the axial direction of not more than about 3 Btu/hr/ft$^2$/° F./ft. The barrier includes electric heating means for heating the tubing to an inner surface temperature sufficient to prevent the growth of microbes thereon. Connector pipes extend axially outwardly from the tubing for mounting the tubing in a drain pipe such that drainage through the drain pipe is required to pass through the tubing. The connector pipes are secured to the tubing by annular insulating rings which isolate the tubing and electric heating means from the connector pipes. The low heat conductivity of the tubing reduces axial transfer of heat from the tubing to supporting drain pipe structures, and the electrically non-conductive nature of the tubing serves as an insulator to prevent the heating means from coming into electrical contact with water or other drainage fluid passing through the tubing.

3 Claims, 5 Drawing Figures

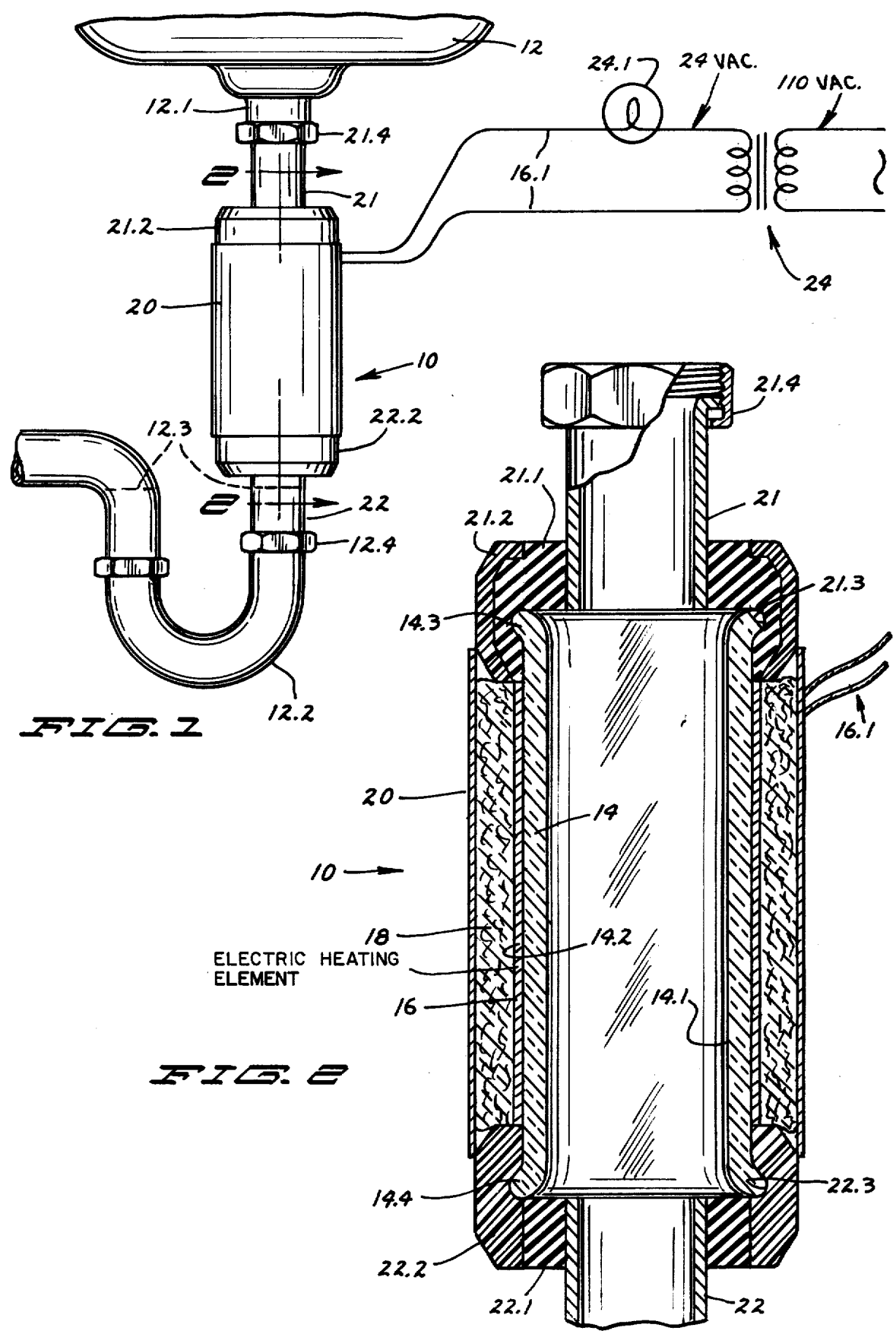

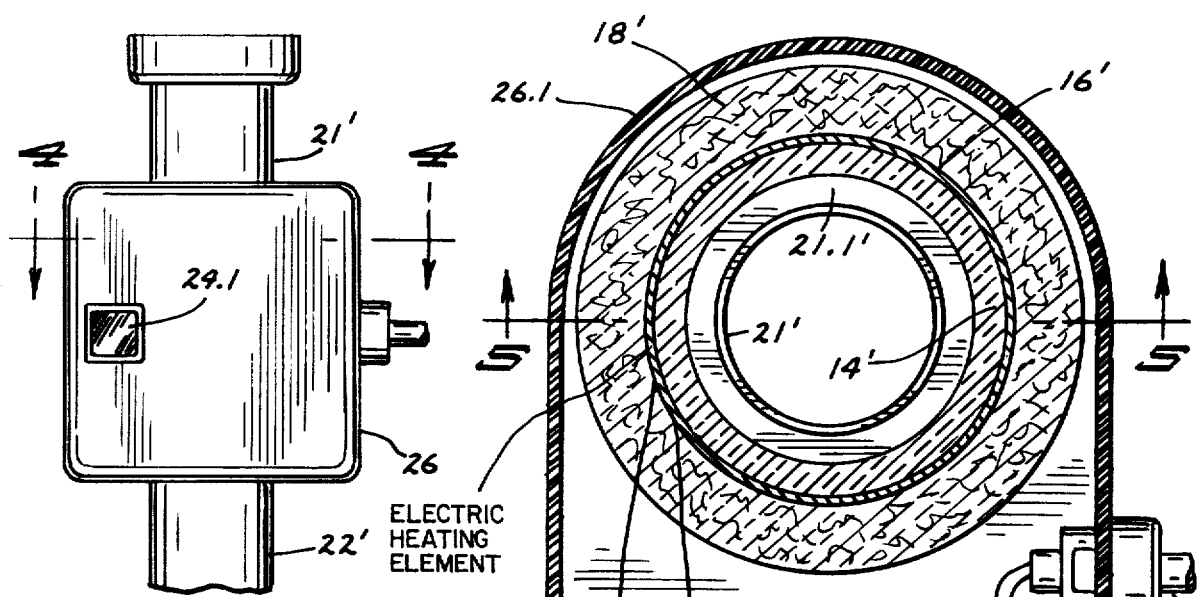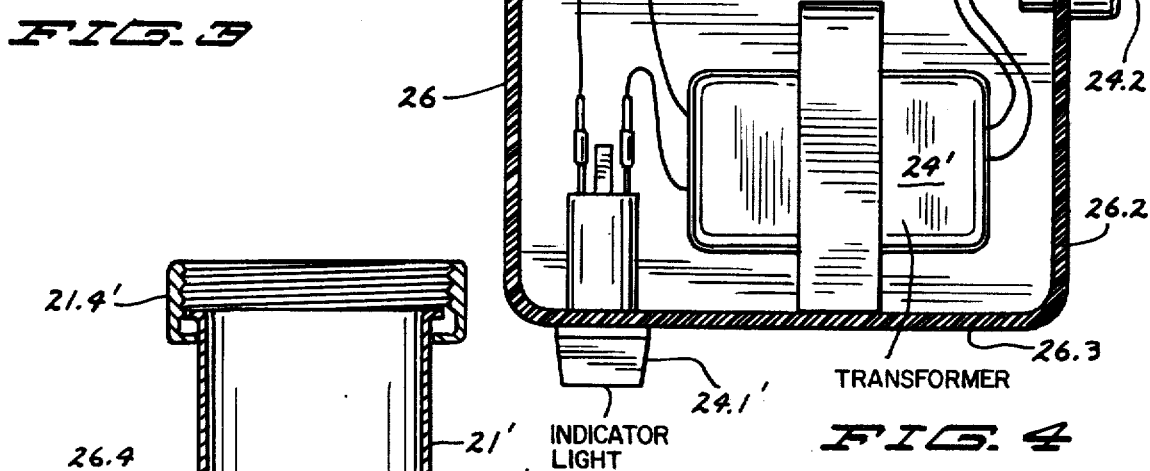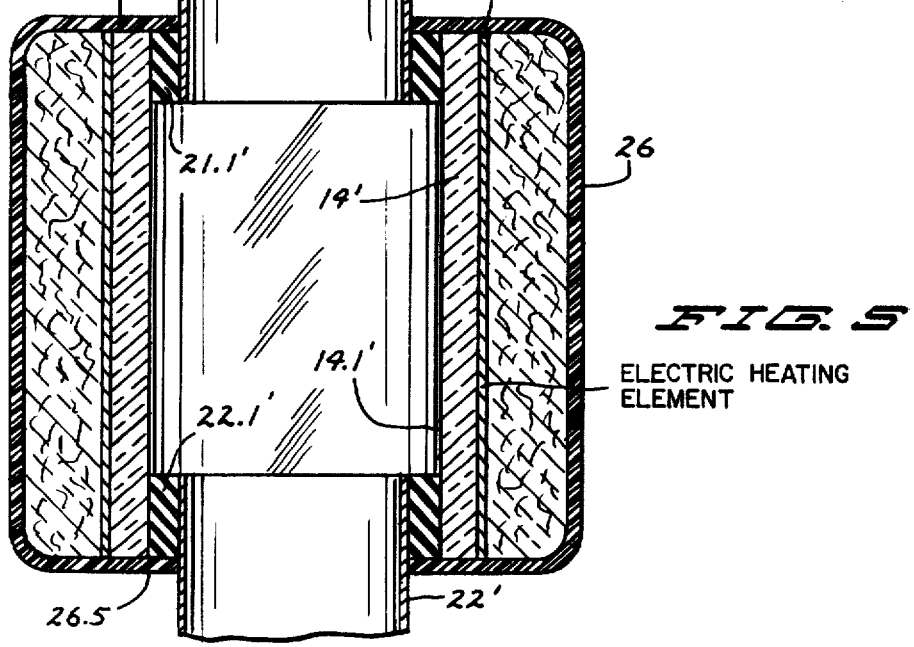

ELECTRICALLY HEATED THERMAL MICROBIAL DRAIN BARRIER

BACKGROUND OF THE INVENTION

In hospitals and clinics particularly, water or other fluids can easily become contaminated with harmful microbes such as E. Coli and the like from the washing of patients or surgical instruments. Such water may then be discharged into a sink for subsequent discharge into a sanitary system. Hospital sinks are often provided with gas traps (known as "P-traps") in drain lines, and the traps may provide excellent breeding grounds for many types of hazardous microbes. Such microbes, when allowed to grow unchecked, may travel upwardly through the sink drain line and into the sink where a susceptable individual may come into contact with them and become infected. The usual gas traps which are employed in drainage systems are often hard to reach and in any event are difficult to sterilize or decontaminate.

Prior art solutions to this problem have involved the use of air gaps in the drain lines of sinks, coupled with drainage holding tanks and pump assemblies, the air gap providing a discontinuous barrier for the return travel of microbes through the drainage system into a sink. Such prior art solutions, it will be understood, have involved the use of expensive and complex equipment. The existence of an air gap in the line, of course, provides a risk that the line may overflow through the air gap.

U.S. Pat. No. 3,985,994 shows an apparatus which can be mounted in the drain of a sink, and which can be heated to prevent the spread of microbes. This device provides a thermal barrier in the form of a heated metal ring into which microbes must come in contact during their travel upwardly into a sink. The ring is electrically heated, and hence the possibility exists of transmitting electricity from the ring to the water in the drain and thence to the sink. In the event the water is contaminated with ionizable materials such as salt, a possibility exists of a user of the sink receiving a shock. Moreover, the heated metal ring may conduct heat rapidly in an axial direction along the drainline in which it is mounted, and further may transfer heat rapidly to water or other drainage fluids passing therethrough.

A thermal barrier for microbes in a drainage system which would require only very small amounts of electric power, which would dissipate heat to the drainage and to adjacent structures only very slowly, and which would serve as an electric insulator between the drainage and the electric heat source, is much to be desired. Desirably, a barrier of this type should be relatively inexpensive and easy to install. It should be substantially maintenance free.

SUMMARY OF THE INVENTION

The present invention provides a thermal microbial barrier for installation in the drain pipe of a sink or the like, and includes a length of thin-walled, heat-resistant, electrically non-conductive tubing having a coefficient of heat conductivity in the axial direction of not more than about 3 Btu/hr/ft$^2$/°F./ft. A preferred material for the tubing is glass. Heating means are provided for heating the tubing to an inner surface temperature sufficient to prevent the growth or travel of microbes thereon. The heating means may take the form of an electric resistance heater in shroud form positioned in exterior circumferential heating proximity to the length of tubing, the tubing itself thus serving as an insulator between the electrical resistance heater and the water or other drainage fluid flowing through the tubing. Mounting means are also provided for mounting the tubing in a drain pipe in such manner as to require drainage through the pipe to pass through the tubing.

DESCRIPTION OF THE DRAWING

FIG. 1 is a side view of a barrier of the invention connected in a drain pipe of a sink, the power source for the device being shown schematically;

FIG. 2 is a broken away, cross sectional view taken along line 2—2 of FIG. 1;

FIG. 3 is a side view of another embodiment of the barrier of the invention;

FIG. 4 is a cross sectional view taken along line 4—4 of FIG. 3;

FIG. 5 is a broken away, cross sectional view taken along line 5—5 of FIG. 4.

DETAILED DESCRIPTION

Referring first to FIG. 1, a sink of the type used in hospitals is shown generally as 12, and is provided with the usual central drain pipe 12.1 and gas trap 12.2 (hereinafter referred to as a "P-trap"). As is known, the P-trap is continuously at least partially filled with stagnant drainage, the upper surfaces of the stagnant drainage pool being shown in phantom lines as 12.3 in FIG. 1. The drain pipe 12.1 is normally continuous downwardly to its connection to the P-trap at the fitting 12.4, and the normally wet interior surface of the drain pipe 12.1 serves as a convenient path for microbes to travel from the stagnant pool in the P-trap upwardly into the sink 12.

The drain barrier of the invention is designated generally as 10 in FIGS. 1 and 2. The barrier is mounted (in the manner to be explained) between the sink 12 and the P-trap 12.2 for the purpose of acting as a barrier to prevent microbes from spreading upwardly from the P-trap into the sink.

Referring now to FIG. 2, the barrier of the invention includes a length of thin walled, heat resistent, electrically non-conductive tubing 14, which preferably is glass. About the exterior surface 14.2 of the tubing is provided an electrical resistance heater 16. Desirably, the heater does not extend the full length of the tubing 14, but rather terminates inwardly slightly from the ends of the tubing. A layer of temperature-resistant insulation 18 is provided about the heater 16, and the insulation is held in place by the means of an outer shroud 20 which may be plastic tubing or the like.

Connecting pipes 21, 22 extend outwardly axially from the open top and bottom of the tube 14, and are connected to the tube by means of annular insulating rings 21.1, 21.2 and 22.1, 22.2, respectively. The outer annular rings, 21.2, 22.2 may be of pre-formed plastic and serve to clamp the inner rings or seals to the ends 14.3, 14.4 of the tubing 14 and the inner rings, 21.1, 22.1 may be formed of a suitable potting compound or may be preformed seals.

It will be noted that the open upper and lower ends 14.3, 14.4 of the tubing 14 are flared radially outwardly slightly to provide a lip which is retained in a suitable annular groove (exemplified as 21.3, 22.3) in the inner surfaces of the rings 21.2, 22.2. In this manner, the rings 21.2, 22.2 can be "snapped" onto the tubing 14 during manufacture.

It will be noted that the inner annular rings 21.1, 22.1 serve to not only mount the connector pipes, 21, 22 to the tubing 14, but also serve to space the connector pipes from the tubing 14. The rings 21.1, 22.1 may be slightly resilient so as to permit the device to be manipulated slightly as it is being installed in a sink drain pipe. It will be understood that the upper end of the connector pipe 21 has the usual drain pipe fitting shown generally as 21.4 for attachment to the lower threaded end of the drain pipe 12.1. The lower end of the connector pipe 22, similarly, may be exteriorly threaded for reception into a similar connector 12.4 of the P-trap 12.2. Other fittings, of course, such as slip fittings or connections, may be used in place of threaded fittings.

The resistance heater 16, which may, simply, be a length of a commercial heating tape wound about the tubing 14, is connected by means of leads 16.1 to the output terminals of a small step-down transformer shown schematically as 24 in FIG. 1 which is in turn connected to a standard 110 volt A.C. line. An indicator light shown as 24.1 may be connected in series in one of the lines 16.1 to show that the heater is in operation. As shown, the electrical power system for the heater preferrably is not thermostatically controled. The amount of heat energy generated in the resistance heater 16 desirably is carefully balanced with the amount of heat loss via heat conduction and radiation so that the temperature of the inner surface 14.1 of the tubing is maintained at a temperature of at least 160° Fahrenheit under steady state heat flow conditions when no drainages passes through the tubing, all as will be more fully described below. It will be understood at this point, however, that the avoidance of employing temperature controls in this system not only renders the invention more economical to produce but in addition avoids a potential major source of equipment failure.

FIGS. 3, 4 and 5 depict a modified embodiment of the invention in which the transformer 24' is enclosed within a housing 26 of heat-resistant plastic or the like, the housing replacing the shroud 20 of the embodiment of FIGS. 1 and 2. The housing 26 in the embodiment of FIGS. 3-5, inclusive, is somewhat elongated in cross section as shown best in FIG. 4. At one end, the walls of the housing are rounded as shown in 26.1 to closly conform with the layer of insulation 18' which in turn is disposed circumferentially about the heating element 16'. The portion 26.2 of the housing which is opposed to the rounded portion 26.1 is spaced away from the insulation as far as is practicable, and has a generally flattened wall 26.3 to the inner surface of which is mounted the transformer 24'. The indicator ligh 24.1 is so mounted in the wall 26.3 as to be clearly visible to a user of the sink in which the barrier is employed. Through a wall of the housing passes a conduit 24.2 terminating in an ordinary electrical plug (not shown) for plugging into an electrical outlet.

With reference to FIGS. 4 and 5, the upper connector pipe 21' is provided at its upper end with a suitable drain pipe connector 21.4'; in similar fashion, the lower end of the lower connector pipe 22' is exteriorly threaded (or provided with a slip-fit end) to receive a similar connection of a P-trap. The open ends of the length of insulating tubing 14' abut and are supported by the inwardly turned upper and lower edges 26.4, 26.5 of the housing, and are spaced radially outwardly from the adjacent portions of the connector pipes 21', 22' by means of annular, insulating spacer rings 21.1', 22.1'. In addition, the inwardly turned edges 26.4, 26.5 of the housing desirably abut and are sealed to the connector pipes 21', 22' as by heat or solvent welding, the connector pipes being made of a suitable material such as rigid plastic or the like to accommodate such sealing. Breather holes (not shown) may be provided in the housing if desired to avoid pressure due to heat build up within the housing. The resistance heater 16, of course, is sufficiently low-powered so as to avoid undue heat buildup.

An important part of the invention resides in the properties of the material of which the tubing 14, is formed. The tubing may be formed of glass, ceramic material, heat and solvent-resistant plastic, or the like, and has a low coefficient of thermal con-ductivity as measured in Btu/hr/ft$^2$/°F./ft. Glass, for example, has a coefficient of thermal conductivity of approximately 0.4, and ceramic materials (such as alumina, clay and the like) have thermal conductivity coefficient values ranging from about 0.5 to about 2.7. Materials suitable for use in the length of tubing 14, desirably have coefficients of thermal conductivity not greater than about 3, measured in the axial direction of the tubing. This is in sharp contrast to the approximate thermal conductivity coefficient values generally reported for copper (218), brass (56) and aluminum (119). In addition, the material of the length of tubing 14, should be electrically non-conductive.

As a result of the low thermal conductivity of the tubing 14, 14', heat which is supplied to the tubing from the resistance heater is lost only very gradually axially to the surrounding structure, and is also only very gradually lost to cold water or other drainage passing through the tubing. The tubing has fairly thin walls, which may be on the order of $\frac{1}{8}$ inch to $\frac{1}{4}$ inch in thickness when the tubing is made of glass. There is no particular desire to heat the water or other drainage flowing through the tubing, but it is desired that the inner surface of the tubing regain its steady state temperature quickly when the flow of drainage is ceased. Because of the poor heat conductivity of the tubing, little heat is lost to drainage flowing through the tubing.

When the flow of drainage stopped, and the tube regains its steady state temperature of at least about 160° Fahrenheit, the inner surface of the tube is quickly dried by evaporation, thereby removing moist breeding places for bacteria and the like. Moreover, at a temperature of approximately 160° Fahrenheit, the growth of dangerous microbes of many types is severely or completely halted and microbes which may remain on the inner surface of the tubing desirably are killed. In any event, the heated inner surface of the tube provides a positive barrier to the travel of microbes upwardly along the inner surface of the tube and into the sink above. In addition, the tubing 14, 14' acts as an electrical insulator between the resistance heater 16 and the water or other drainage flowing through the tube, thereby preventing an electric current from the heater from passing through the tubing into contact with the drainage which could cause serious or at the very least irritating shocks.

As best described, the thermal microbe drain barrier of my invention is relatively inexpensive to manufacture and use, and can easily be installed in existing sink drain pipes. Because of the low value of the coefficient of thermal conductivity of the tubing 14, heat loss to drainage and to supporting structures is minimized, and the thermal barrier can thus operate efficiently on only very small amounts of electric power.

What is claimed is:

1. In combination with a sink or the like having a drain pipe, a thermal microbial drain barrier for preventing microorganisms from reentering the sink through the drain pipe and comprising a length of thin-walled, heat-resistant, electrically non-conductive tubing having a heat conductivity in the axial direction of not more than about 3 Btu/hr/ft$^2$/°F./ft;

electric heating means positioned exteriorly of and in circumferential heating proximity to the tubing for heating the tubing, in the absence of drainage flow, to an inner surface temperature sufficient to prevent growth of microorganisms thereon, the tubing electrically insulating the electric heating means from the inner surface of the tubing; and mounting means mounting the tubing in the drain pipe in a manner requiring drainage from the sink or the like to pass through the tubing, the mounting means comprising connector pipes extending axially outwardly from the tubing and connecting the latter into the drain pipe of the sink or the like, and means joining the connector pipes to the tubing including insulating means electrically insulating the pipes from the electric heating means and thermally insulating said tubing from the connector pipes.

2. The combination of claim 1 including a housing enclosing the tubing and electric heating means; a transformer for powering the heating means; means connecting the transformer to a source of power; the housing sealingly engaging about the circumference of the connector pipes to provide a sealed, generally waterproof unit.

3. In combination with a sink or the like having a drain pipe, a thermal microbial drain barrier preventing microorganisms from reentering the sink through the drain pipe and comprising a length of thin-walled, heat-resistant, electrically non-conductive tubing having a heat conductivity in the axial direction of not more than about 3/Btu/hr/ft$^2$/°F./ft;

an electrical resistance heater positioned exteriorly of and in circumferential heating proximity to the tubing and capable of heating the tubing, in the absence of drainage flow, to an inner surface temperature of at least about 160° F.;

mounting means comprising connector pipes extending axially outwardly from the tubing and connecting the latter into the drain pipe in a manner requiring drainage from the sink to pass through the tubing;

insulating means electrically insulating the connector pipes from the heater and thermally insulating the tubing from the connector pipes; and a generally waterproof housing enclosing the tubing and resistance heater and sealingly engaging about the circumference of the connector pipes.

* * * * *